United States Patent [19] [11] 4,255,049
Sahm et al. [45] Mar. 10, 1981

[54] NON-DESTRUCTIVE TESTING OF STRUCTURAL ELEMENTS FOR FATIGUE BY MEASUREMENT OF SPECULAR REFLECTANCE

[75] Inventors: Karl-Frieder Sahm, Immenstaad; Enno van Rensen, Uhldingen-Muehlhofen; Horst Rieger, Immenstaad; Franz Jaeger, Stetten, all of Fed. Rep. of Germany

[73] Assignee: Dornier System GmbH, Friedrichshafen, Fed. Rep. of Germany

[21] Appl. No.: 957,168

[22] Filed: Nov. 2, 1978

[30] Foreign Application Priority Data

Nov. 8, 1977 [DE] Fed. Rep. of Germany ....... 2749836

[51] Int. Cl.$^3$ ............................................. G01B 11/16
[52] U.S. Cl. ......................................... 356/32; 73/762
[58] Field of Search ................ 356/32, 34, 35; 73/762

[56] References Cited

U.S. PATENT DOCUMENTS

| 3,272,003 | 9/1966 | Harting. | |
| 3,462,223 | 8/1969 | Tiemann et al. | 356/32 |
| 3,715,915 | 2/1973 | Williams | 356/32 |
| 4,015,465 | 4/1977 | Scott | 356/32 |

FOREIGN PATENT DOCUMENTS 2063913 12/1973 Fed. Rep. of Germany.
2417232 11/1975 Fed. Rep. of Germany ............. 356/32

OTHER PUBLICATIONS

"Luftfahrttechnik/Raumfahrttechnik", vol. 14, Jul.-/Aug. 1968, p. 196.

Primary Examiner—Vincent P. McGraw
Attorney, Agent, or Firm—Toren, McGeady and Stanger

[57] ABSTRACT

Fatigue in structural elements is determined by measuring the loss in specular reflection in a foil of polished metal secured to an exposed surface of the tested object, the elastic limit of the foil material under shearing stresses being lower than that of the tested object, and the foil consisting either of a single crystal or of polycrystalline material of uniform, small grain size.

6 Claims, No Drawings

NON-DESTRUCTIVE TESTING OF STRUCTURAL ELEMENTS FOR FATIGUE BY MEASUREMENT OF SPECULAR REFLECTANCE

This invention relates to the non-destructive testing of objects for fatigue, and particularly to fatigue testing by measuring the loss in specular reflectance in polished foils secured to an exposed surface of the tested object.

It is known from the commonly owned German Pat. No. 2,417,232 that a thin, crystalline metal strip or foil fastened to the surface of a test object in area contact and having an exposed major surface of high reflectance loses specular reflectance when the surface of the test object is subjected repeatedly to shearing stresses within its elastic limit which exceeds the elastic limit of the strip. The loss of specular reflectance of the surface thus may be correlated with known fatigue properties of the test object to predict remaining useful service life.

It has now been found that the known method yields precisely reproducible results when the material of the metal foil is either a single crystal or consists of a multiplicity of crystals of very small, uniform size. Such foils are sensitive to very few repeated stresses in the tested substrate which result in strains as small as 1:10,000. Particularly, foils consisting of single crystals of metals of high purity permit the loss of specular reflectance to be measured with great precision so that results achieved on one known substrate fully characterize the response of the foil, and permit the standardized foil to be employed on other materials without requiring calibration. Similar advantages are achieved with polycrystalline metal foils whose grain structure is distinguished by uniformity and small size of individual crystalites.

For highest precision, the metallic materials of the foils should consist of 99.99% of a single metal. However, more reproducible results than were available heretofore can be achieved with less pure metals whose impurities are closely defined as to chemical nature and amounts, and carefully prepared alloys are also useful. They are preferably limited to two major components.

The metals preferred for use in the foils of the invention are distinguished by insignificant, permanent hardening when plastically deformed at or near their expected operating temperature. For use of room temperature of about 20° C. and below, the preferred metallic foil materials are aluminum, tin, indium, zinc, gold, silver, cooper, lead, nickel and titanium of highest purity. For use at elevated temperature, as in steam or gas turbines, metals of higher melting points are necessary, and cobalt, chromium, vanadium, titanium, molybdenum, tellurium, tantalum, gold, nickel, cooper, and silver may be considered, the specific selection being controlled by the ability of the foil material to undergo plastic deformation at the prevailing operating temperature within the range of strains occurring in the substrate.

The thickness of the foils employed is preferably between 10 and 100 μm and must be controlled precisely if reproduciblity is essential.

Test pieces may be prepared for storage prior to use from suitable foil material by the following steps, though not necessarily in the sequence indicated:

(1) Polishing of one major surface of a piece of foil larger than the required test piece and in the fully annealed condition.
(2) Cutting of the polished foil into individual test pieces.
(3) Smoothing of cut edges.
(4) Heat treatment to eliminate hardening, if any, by the polishing and cutting steps.
(5) Application of a carrier to the non-polished surface for mechanical reinforcement against damage in handling.
(6) Application of a protective layer on the polished surface.

Because fatigue in a tested object is measured by the loss of specular reflectance of the polished test piece surface, a reproducible polishing method is preferred. The foil to be polished may be fastened on a smooth, planar supporting surface by means of an adhesive which permits release under mild conditions. Molten paraffin is the preferred adhesive. The exposed surface then is polished mechanically, as by vibration polishing. When the foil is fastened on a very strong carrier prior to polishing, a rapidly rotating fabric wheel may also be employed. Electrolytic polishing and chemical polishing also has been used successfully when the results were monitored carefully.

The fully soft starting condition of the foil material is preferably established by heat treatment, typically for 30 minutes to two hours at approximately ½ to ¾ of the melting temperature, as measured in degrees Celsius. The treatment should cause recrystallization of polycrystalline foil material if used. Corresponding heat treatment is resorted to for removing the hardening caused by mechanical polishing and/or smoothing of cut edges.

Suitable carriers stronger than the test pieces are plastic foils having a thickness of 20 to 150 μm, also hardened metal foils of high elasticity, that is, showing a length change of at least 1% if stressed in tension to the proportional limit. The carrier may be affixed to the foil material prior to cutting individual test pieces, or the cut pieces may be secured to the carrier. In performing a fatigue test, the exposed surface of the carrier is fastened to the tested object in area contact.

The polished surface of the test piece is preferably protected against loss of reflectance during storage, transportation, and mounting operations by a foil of synthetic resin composition carrying a thin layer of pressure-sensitive adhesive. The bond between the protective foil and the polished surface should be extremely weak, consistent with the handling stresses to be applied, so that removal of the protective layer does not alter the mechanical and optical properties of the test piece.

The test piece is mounted on the tested object either in direct area contact or indirectly by a carrier, and adhesives are merely representative of the materials employed for producing a bond which is unaffected by the stresses to be transmitted from the tested object to the test piece. Depending on the nature of the foil material, soft and hard soldering, plating, and even diffusion welding may be resorted to.

When the surface of the tested object to which the test piece is to be affixed is of arcuate cross section, it is preferred to employ an intermediate layer of material whose face directed toward the tested object conforms to the arc of the substrate surface, while the face carrying the test piece is planar. Such an arrangement avoids the errors in the measurement of specular reflectance which would otherwise be unavoidable.

After having been fastened to the tested object in direct or indirect area contact, the test foil may be protected during storage of the tested object or during fatigue-generating service by coatings applied to the polished surface. Protection prior to reflectance measurement may be afforded by sheet material having a cushioning effect and secured by means of pressure-sensitive adhesive (felt, cellular rubber or plastics, muslin, and the like), a peelable layer of synthetic resin composition applied by spraying or brushing, a removable rigid cover. For protection against chemical and mechanical stresses other than the fatigue-generating stresses to be measured, a firmly adhering, transparent layer of plastic may be applied and remain in place during service if it does not interfere with reflectance measurement. An opaque, reflecting material may be employed in the same manner if its change in reflectance reproducibly reflects the change in the test piece.

The direction of the principal shearing stresses in the substrate can be determined by the use of test pieces of anisotropic material. Monocrystalline foils show different mechanical properties due to anisotropy of the crystal lattice, and anisotropy in polycrystalline rolled foils is observed even after heat treatment.

Other features, advantages, and applications of the invention will become apparent from the following illustrative Examples. All tests were performed on sheet material of various aluminum alloys which constituted skin portions of an airplane wing subject to repetitive shearing stresses of different magnitude and amplitude in normal service.

EXAMPLE 1

Fatigue-generating stresses of a relatively low level were measured by means of single-crystal foils of practically pure (99.99% or better) aluminum, tin, and indium having a thickness of 50 $\mu$m. The test pieces were cut from larger pieces of polished foil. The starting materials were in the fully soft condition and were attached to a hot, polished support covered with molten paraffin when the support was cooled to room temperature. The fastened foils were polished by means of alumina and a vibrator, and were then released from the support by heating the latter. Pieces approximately 1 cm$^2$ in size were cut from the polished foils, care being taken to maintain a known angular relationship between the cut edges and the lattice planes of the foil so that the test pieces could be affixed to the test object for greatest sensitivity in the direction of one of the principal shearing stresses.

After being cut to size, the test pieces were annealed until their original soft condition was restored, the selected temperatures being approximately 350° C. for the aluminum foil, about 100° C. for the tin foil, and approximately 50° C. for the indium foil. The polished surfaces were covered with plastic foil carrying pressure-sensitive adhesive until ready for service. The test pieces were attached to the selected portion of the airplane wing by means of adhesive after both contact areas had been cleaned thoroughly with trichloroethylene. The adhesive employed was a commercial product, a two-component epoxide adhesive which cured rapidly after mixing and was insensitive to the ambient atmosphere and water. The plastic foil was removed from the polished surface of the attached test piece, and an initial reading of specular reflectance was taken by means of a commercial reflectometer of a conventional type more fully described and illustrated in the afore-mentioned German patent.

Thereafter, the test piece was protected against environmental factors affecting reflectivity by means of plastic sheeting coated with pressure-sensitive adhesive and carrying a central pad of felt. The felt was applied loosely to the polished surface, and the annular, exposed area of adhesive-coated sheeting was fastened to the wing surface about the test piece. It was removed from time to time when the reflectance changes in the test piece were to be measured.

Similar protection could be achieved by mounting a rubber ring on the surface of the tested object in such a manner as to spacedly envelop the test piece. The chamber thus bounded by the ring was closed by a metal cover between measurements.

EXAMPLE 2

Polycrystalline foils of high-purity aluminum, tin, and indium were employed for indicating repetitive shearing strains in other portions of the wing under service conditions similar to those described in Example 1. The grain size of the aluminum foil was less than 0.5 mm and as uniform as could be determined. The foils had been produced by rolling and subsequent annealing, and they were fastened to the substrate in such a manner that the direction of grain elongation still visible after annealing coincided with the direction of the expected principal strains in the substrate.

EXAMPLE 3

Portions of the wing surface subjected to more intense stresses and undergoing corresponding shearing strains were tested in the manner described above by means of foils containing 99.5% aluminum, tin, and indium respectively, together with precisely dosed minor ingredients, also 99.99% nickel, gold, silver, titanium, and copper and binary alloys such as aluminum containing 6% silicon.

When mechanical polishing was avoided, and the desired reflectance was achieved by electropolishing or chemical polishing, the hardening unavoidably produced by the mechanical treatment did not occur, and a secondary heat treatment became unnecessary. For greater reproducibility, the surface later to be fastened to the tested object was covered with conventional stop-off lacquer prior to polishing. The cutting of test pieces from the previously polished larger foil did not produce a hardening of the foil material which needed to be removed where extreme requirements as to precision did not have to be met. In such instances, it was also more convenient to anneal the large pieces, as mechanically polished, and to cut test pieces from the annealed material. A carrier sheet not affected by the annealing was attached to the foil material prior to polishing and was cut together with the latter to the desired size.

EXAMPLE 4

Eight test pieces were prepared as in Example 2 from foil material having anisotropic mechanical properties and were mounted on a portion of the wing skin in which the direction of the principal strains was to be determined. The test pieces were arranged in such a manner that their known directions of greatest sensitivity diverged from a central point on the tested area at angles of about 45°. From the different rates at which the several test pieces lost their brightness, the directions of the principal strains in the substrate, as well as their magnitudes, were readily determined.

Structural elements operating at temperatures much above 20° C. in oxidizing or otherwise corrosive atmospheres were tested by means of foils consisting of aluminum, nickel, gold, chromium, cobalt, titanium, and silver selected to resist the prevailing temperature and atmosphere. Organic adhesives could not be employed for mounting these foils, and soft or hard soldering and diffusion welding were resorted to in a basically known manner.

It should be understood, therefore, that the foregoing disclosure relates only to preferred embodiments of the invention, and that it is intended to cover all changes and modifications of the examples herein chosen for the purpose of the disclosure which do not constitute departures from the spirit and scope of the invention set forth in the appended claims.

What is claimed is:

1. A non-destructive method of testing an object for repetitive stresses which comprises the steps of applying to a stressed surface portion of said object one major face of at least one piece of a single crystal foil material in area contact, the other major face of said foil material being polished to high specular reflectance, and measuring the reduction of said specular reflectance after application of said stresses to said object, said foil material having an elastic limit lower than the elastic limit of the material of said surface portion, and lower than the stresses transmitted to said foil material from said surface portion.

2. A non-destructive method of testing an object for repetitive stresses which comprises the steps of applying to a stressed surface portion of said object one major face of at least one piece of a foil material in area contact, the other major face of said foil material being polished to high specular reflectance, and measuring the reduction of said specular reflectance after application of said stresses to said object, said foil material having an elastic limit lower than the elastic limit of the material of said surface portion, and lower than the stresses transmitted to said foil material from said surface portion, wherein said foil material is polycrystalline, the crystals in said material being not greater than 0.5 mm and substantially uniform in size.

3. A method as set forth in claims 1 or 2, wherein a plurality of said pieces is applied to said surface portion, each of said pieces being most sensitive to said transmitted stresses in a predetermined direction, the predetermined directions being angularly offset from each other in the applied pieces.

4. A method as set forth in claims 1 or 2, wherein said surface portion is of arcuate cross section, a body being interposed between said surface portion and said one major face in conforming, stress-transmitting engagement with said surface portion and with said one major face, said one major face being substantially planar.

5. A method as set forth in claims 1 or 2, wherein said foil material has a thickness of 10 to 100 $\mu$m.

6. A method as set forth in claims 1 or 2, wherein at least 99.99% of the weight of said foil material consists of aluminum, indium, or tin.

* * * * *